(12) United States Patent
Farber et al.

(10) Patent No.: US 11,053,608 B2
(45) Date of Patent: Jul. 6, 2021

(54) COMBINATORIAL DERIVATIVES OF RNA OLIGONUCLEOTIDES

(71) Applicants: Boris Farber, Brooklyn, NY (US); Sof'ya Farber, Brooklyn, NY (US); Artur Viktorovich Martynov, Kharkov (UA)

(72) Inventors: Boris Farber, Brooklyn, NY (US); Sof'ya Farber, Brooklyn, NY (US); Artur Viktorovich Martynov, Kharkov (UA)

( * ) Notice: Subject to any disclaimer, the term of this patent is extended or adjusted under 35 U.S.C. 154(b) by 0 days.

(21) Appl. No.: 16/771,364

(22) PCT Filed: Jun. 16, 2017

(86) PCT No.: PCT/RU2017/000423
§ 371 (c)(1),
(2) Date: Jun. 10, 2020

(87) PCT Pub. No.: WO2018/231090
PCT Pub. Date: Dec. 20, 2018

(65) Prior Publication Data
US 2021/0071317 A1 Mar. 11, 2021

(51) Int. Cl.
*C40B 40/06* (2006.01)
(52) U.S. Cl.
CPC ................................. *C40B 40/06* (2013.01)
(58) Field of Classification Search
None
See application file for complete search history.

(56) References Cited

U.S. PATENT DOCUMENTS

| 5,614,617 | A | 3/1997 | Cook et al. | |
| 6,867,290 | B2 * | 3/2005 | Goldsborough | ....... C07H 21/00 435/6.1 |
| 2012/0130060 | A1 | 5/2012 | Martynov et al. | |
| 2014/0309276 | A1 * | 10/2014 | Martynov et al. | ............ A61K 31/7088 514/44 A |

* cited by examiner

*Primary Examiner* — Kaijiang Zhang
(74) *Attorney, Agent, or Firm* — Daniel M. Cohn; Howard M. Cohn

(57) ABSTRACT

Field of application: This invention relates to the chemistry of nucleotides and allows to synthesize new combinatorial libraries of supramolecular oligonucleotides for use in medical fields, cosmetology and pharmaceutical industry. This invention also can be applied for the creation of means used in the body rejuvenation, treating human diseases such as cancer, trophic ulcers, creating new herbicides and pesticides.

The essence of the invention Combinatorial derivatives of RNA oligonucleotides, wherein for their production, covalent modification of the initial RNA oligonucleotides is carried out by simultaneous combinatorial carboxylation and formylation of the exocyclic amino groups of adenine, guanine, cytosine and the ribose alcohol residue in the reaction with the maximum number of different synthesis derivatives, and as a result of synthesis, a combinatorial mixture of derivatives of each oligonucleotide is formed and then use the resulting combinatorial mixture as a whole without fragmentation to create biologically active compositions.

14 Claims, 5 Drawing Sheets

COMBINATORIAL DERIVATIVES OF RNA OLIGONUCLEOTIDES

TECHNICAL FIELD

This invention relates to the nucleotides chemistry and it allows to synthesize a new combinatorial libraries of supramolecular oligonucleotides, which will be used in medical field, cosmetology and pharmacology, treating human diseases such as cancer and trophic ulcers, including entire body rejuvenation agents, and even creating new herbicides and pesticides in agriculture field.

STATE OF THE ART

Combinatorial chemistry, the methodology of organic chemical synthesis, which is necessary for synthesis a large array of chemical compounds of the same type (combinatorial libraries) in the fastest and most economical way, using specific approaches and technologies.

The need for the synthesis of extensive combinatorial libraries arose in the 1990's and was dictated by the requests of those industries where the search for substances with useful properties is often more effective by empirical enumeration of properties on a large samples of compounds of the same type. The basis for the development of a new direction of chemical synthesis was the solid-phase peptide synthesis proposed by R. Merrifield.

Methods of combinatorial chemistry are especially used in pharmaceuticals (new drugs design), in the search for effective catalysts (polymerization, etc.), in the design of nanomaterials. For testing combinatorial libraries, automated robotic systems have been developed, the productivity of which reaches 100 thousand samples per day (the so-called high performance screening).

In practice, combinatorial chemistry is a set of techniques and methods for combining diverse initial chemical reagents to obtain the most diverse arrays of chemical products by conducting tens, hundreds, and sometimes thousands of parallel chemical transformations with the formation of a huge number of final products.

Combinatorial chemistry solves problems, which is rarely arising in classical chemical synthesis, namely, to quickly synthesize many substances, usually complex in structure and sufficiently pure. The development of new economical and high-speed technologies for parallel synthesis and parallel purification of substances is achieved in a variety of ways.

Instead of the standard liquid-phase synthesis (one substance in one vessel at a time), a lot of syntheses are put (for example, in a plastic plate with many cells, where the substances are introduced by multichannel pipettes). Instead of boiling under a reflux, they use the heating of multiple sealed capsules (in a cellular thermostat or microwave oven). To filter multiple substances using "filter vessels" (for example, dies with a porous bottom).

Evaporation is carried out by vacuum freezing of the solvent from centrifuged (to prevent foaming) diy. For purification using methods of parallel chromatography, combining in blocks of many chromatographic columns. In methods of liquid-phase combinatorial chemistry, they try to use only those reactions that proceed in high yields and require minimal effort to purify the substances. In order to achieve a wider variety of products, conventional two-component reactions are replaced by multicomponent ones.

A powerful technology of combinatorial chemistry is solid-phase synthesis—carrying out reactions on a modified polymer substrate. In this case, a complex molecule (for example, a polypeptide of the desired sequence or a complex heterocyclic compound) is immobilized ("built up") on the surface of the polymer during the sequence of reactions, and then, at the final stage, is cleaved from the solid substrate due to any chemical transformations.

Therefore, reactions can be carried out with a large excess of reagent, washing the latter from the polymer with the target substance and reducing the synthesis to the principle of "tea bag" (porous bags with polymer granules are sequentially placed in glasses with reagents).

A new technology is the replacement of solid polymers with perfluorinated liquids (not miscible with water and standard solvents). For immobilization (transfer of the substance to the perfluorinated phase), an extended perfluoroalkyl moiety is attached to the molecule of the starting reagent. This allows the synthesis in emulsions, followed by separation of the liquid phases.

The combined method of combinatorial chemistry is the use of solid-phase reagents (oxidizing agent, acid, base are immobilized on a polymer). Excess solid reagent is added to the solutions of substances, and then separated by filtration.

Another technique is using of so-called scavengers—a modified polymer is added to the solution, which selectively removes excess reagent from the reaction mixture. Programmed industrial robots are being used more often lately. They are performing a sequence of routine, uniform procedures for the isolation and purification of substances (automatic synthesizers). The effectiveness of the use of combinatorial chemistry is proved by the examples of the discovery of new drugs and catalysts.

Ref.: Accounts of Chemical Research. 1996. Vol. 29. No. 3; Chemical Reviews. 1997. No. 3-4; Handbook of combinatorial chemistry: drugs, catalysts, materials. Weinheim, 2002. Vol. 1-2; Combinatorial chemistry on solid supports. B., 2007.

The Use of Substance's Combinatorial Libraries is a Relevance.

One of the new directions in the treatment of cancer is the development of gene therapy for cancer.

One of the most promising areas of gene therapy is a means for inactivating genes based on complementary polynucleotides.

One of the main problems on the way of introducing cancer gene therapy is the destruction of synthetic complementary nucleotides by blood nucleases, also limited penetration into cells, and sensitivity to cell genome repair systems.

There are different approaches to design antisense oligonucleotides, but the principle of their interaction with targets remains the same: the formation of hydrogen bonds between complementary nucleotides with an increase in the degree of resistance to nucleases.

In some cases, the developers protected the 5'-end of the oligonucleotide from the action of nucleases, in others, they modified the 3'-end. US Scientists have replaced deoxyribosyl residues to morpholine fragments in order to create DNA fragments (RNAs) resistant to the action of nucleases. At the same time, the principle of gene inactivation through their complementary interaction with antisense nucleotides remained the same—the formation of hydrogen bonds. They also known are complementary miRNAs, which are selectively blocking the synthesis of certain proteins in the cell.

It is well known that many adenocarcinomas capture oligonucleotides and nanoparticles through pinocytosis. At the same time, healthy cells are not able to capture small oligonucleotides and liposomes.

This ensures selective accumulation of the proposed protected oligonucleotides (modified anti-tRNA—MATR) in cancer cells and the absence of toxicity of the MATR composition. To obtain MATR, we used oligomeric fragments of tRNA—recognized by ribosomes. This oligo-RNA gave the property of complementarity and protection against nucleases by simultaneous combinatorial formylation and acylation without subsequent separation of the combinatorial library into individual compounds.

Selective accumulation of the MATR in the cancer cell leads to cancer cell hybridization with complementary targets in the tRNA of the cancer cell and to a gradual halt in protein synthesis due to the blockade of protein synthesis in the phase of incorporation of amino acids into the polypeptide chain.

The action of MATR is based on the induction of apoptosis through the termination of protein synthesis. MATR actually does not affect healthy cells, blocks the synthesis of all cancerous cellular proteins, excludes the adaptation of the cancerous tumor to therapy and the selection of resistant cells due to the excessive number of combinatorial RNA fragments and the inability of the tumor to adapt to such a huge number of fragments.

In addition to antitumor activity in vitro, MATR also showed high in vivo activity in mice models of Ehrlich ascites adenocarcinoma, mouse Lewis carcinoma (a powerful antimetastatic effect by reducing 50% the number of metastases and halving the size of the central tumor), and prolonging mice's lifespan.

Terminology

Complementarity—(in the genetics and chemistry of nucleic acids)—the property of nitrogenous bases to form adenine—thymine (or uracil) and guanine—cytosine paired complexes by means of hydrogen bonds in the interaction of nucleic acid chains.

Complementary oligonucleotides (antisense)—chain B, complementary chain A of the original oligonucleotide, capable of special hybridization to chain A.

DNA hybridization (RNA)—the formation of double-stranded DNA (RNA) or DNA:RNA duplexes as a result of the interaction of complementary nucleotides.

Inactivation of genes—disabling the process of gene expression through process of hybridization with a complementary strand of RNA or DNA.

DNA repair—repairing damaged DNA molecule, restoring its original structure, it is believed that the cancer cell genome repair system is responsible for both the resistance of cancer cells to classical chemotherapy drugs based on antimetabolites of mononucleotides and the survival of the tumor cells during massive chemotherapy and the high initial sensitivity of the tumor to treatment.

Adenocarcinomas—is a type of cancerous tumor that is defined as neoplasia of epithelial tissue that has glandular origin, glandular characteristics, or both. (accounts for more than 80% of all types of cancer)

Blood nuclease—blood enzymes that are destroing free RNA and DNA in the blood to mononucleotides.

Formylation is the process of attaching the remainder of formic acid to amino groups, alcohol groups with the formation of the remainder of the aldehyde group. There are many named reactions of formylation (Duff reaction, Hatterman reaction, Huben-Gösch reaction, Hatterman-Koch reaction)

Acylation—the introduction of the acyl residue of RCO- (acyl) into the organic compound, as a rule, by replacing the hydrogen atom, the introduction of the residue of acetic acid $CH_3CO$—is called acetylation, benzoic $C_6H_5CO$—benzoylation, formic HCO—formylation. Depending on the atom to which the acyl residue is attached, C-acylation, N-acylation, O-acylation are isolated. As acylating agents, acid halides and acid anhydrides are used.

Alkylation—the introduction of an alkyl substituent in an organic compound molecule. Typical alkylating agents are alkyl halides, alkenes, epoxy compounds, alcohols, less often aldehydes, ketones, esters, sulfides, diazoalkanes. The alkylation catalysts are mineral acids, Lewis acids, and also zeolites. Alkylation is widely used in the chemical and petrochemical industries.

Micro-RNAs are small non-coding RNA molecules 18-25 nucleotides long (on average 22), found in plants, animals, and some viruses that are involved in transcriptional and post-transcriptional regulation of gene expression by RNA interference. In addition to intracellular, extracellular (circulating) microRNA was detected.

Combinatorial synthesis—synthesis by methods of combinatorial chemistry, involves the simultaneous reaction between three or more reagents with the formation of a combinatorial synthesis products, consisting of dozens of derivatives. These derivatives are then separated chromatographically, confirmed their structure and studied the biological activity.

Simultaneous combinatorial modification with two modifiers—if a multifunctional molecule with more than two groups available for modification is used in the combinatorial synthesis reaction and two modifying agents are introduced immediately, for example, acetic anhydride and succinic anhydride. As a result of the reaction, a mixture of acylated derivatives in different positions—acetyl-succinyl derivatives—is formed.

The combinatorial library [lat. combinare—connect, combine; Greek biblion—book and theke—repository]—a set of a large number of various chemical compounds, proteins, genes or oligonucleotides, allowing you to quickly search for target genes or target proteins. For example, a kit consisting of millions of different chemicals, or a set of recombinant DNA molecules, obtained by incorporating various antibodies into the light and heavy chains of a cDNA vector, etc.

Known oligonucleotides containing modified and unnatural nucleotide bases [1]. The mechanism of action of the patented oligonucleotides was similar to antisense RNA and micro RNA, and drugs could be used in the treatment of including cancer.

The disadvantage of patentable oligonucleotides is a complex multi-stage and expensive synthesis of RNA derivatives, which is difficult to reproduce in an industrial environment.

In addition, the method patented in the prototype did not allow to obtain combinatorial mixtures from thousands of derivatives capable of preventing the effect of addiction or mutation of the target.

The use of the object of this patent was not effective in experiments on animal models for cancer, in addition, this development is more applicable for diagnostic and screening studies in vitro than to create drugs for the treatment of animals and humans due to the fact that the proposed modification of the nucleotide bases are new xenobiotics and are not subject to safe metabolism and biodegradation in the body. Known modified anti-complementary oligonucleotides with anticancer properties and a method for their preparation [2].

The essence of the invention: modified anti-complementary oligonucleotides with anticancer properties and a method for their preparation, characterized in that the oligonucleotides are a mixture of products of hydrolysis of polynucleotides, and the modification is carried out by reversing the sign of the charges of the nucleotide base molecules, which acquire anti-complementary properties.

The hydrolysis of polynucleotides is carried out using natural or synthetic nucleases, acid or alkaline hydrolysis, and the structure is modified by acylating the amino groups of the mononucleotides in the structure of the oligonucleotides with dicarboxylic acid anhydrides or by alkylation with halocarboxylic acids.

The developed mixture has the ability to selectively bind to tRNA and thereby stop protein synthesis in cancer cells, similar to the action of miRNAs. The use of the drug in connection with its ability to adapt to the body allows you to overcome the addiction of the tumor to the drug.

This invention has a wide spectrum of action, low toxicity and is available for industrial production, effectively at all stages of the cancer process. The disadvantage of this invention is the inconstancy of the composition of the initial RNA for modification and, accordingly, the inconsistency of the pharmacological effect of the final product, the difficulty of standardizing it, the presence of enzyme residues—ribonuclease, the presence of only one chemical mechanism of interaction with tRNA of cancer cells through ionic bonds. In this regard, the effect of such a composition is unstable and tumor growth stopes for short period of time.

These shortcomings are eliminated by using two modifiers at once—allowing to use not only ionic bonds between carboxyl and amino groups in complementary fragments, but also hydrogen bonds, to significantly increase the number of derivatives, eliminating the adaptation of the tumor to the drug; the use of oligonucleotides originally with clearly known sequences, which greatly simplifies their standardization, validation, registration and allows complete chemical synthesis on nucleotide synthesizers; allows to ensure the repeatability of pharmacological effects between series.

In addition, the use of such binary modified oligonucleotides significantly prolongs the pharmacological effect of the drug in the form of a longer effect (survival of mice). Previously, double simultaneous modification of RNA and DNA oligonucleotides was not used.

DISCLOSURE OF INVENTION

The basis of the invention is the task to develop biologically active combinatorial derivatives of RNA oligonucleotides (combinatorial libraries).

The problem is solved by obtaining a mixture of complementary combinatorial derivatives of RNA oligonucleotides in which the property of complementarity and protection against nucleases is imparted by the simultaneous double combinatorial formylation and carboxylation (acylation or alkylation) of exocyclic amino groups of mononucleosides and alcohol residues in the ribose structure of the RNA according to the scheme:

Nz-NH$_2$ + HCOOH = Nz-NH—COH
(formylated nucleoside exocyclic amino groups)

Nz-NH$_2$ + R—COOCO—X— = Nz-NH—COR
(acylated exocyclic amino groups of the nucleoside)

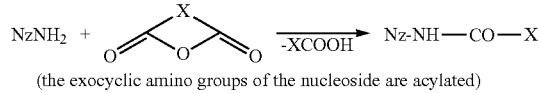
(the exocyclic amino groups of the nucleoside are acylated)

-continued

(the exocyclic amino groups of the nucleoside are acylated)

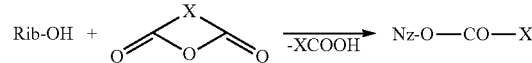
(the acylates free ribose residue in the structure of RNA)
(the free ribose residue alkylated in the RNA structure)
R—OH + HCOOH = R—O—COH (ribose residue goes through the process of formylation)
Nz-nucleoside residue in the structure of alanine tRNA oligonucleotides
Rib-ribose residue in the nucleoside structure of the alanine tRNA oligonucleotides
X-closed hydrocarbon chain in the structure of dicarboxylic and tricarboxylic acid anhydrides The combination of composition mixture is not purified to separate components, but is used entirely as an anticancer drug to prevent the adaptation of the tumor or to create pharmaceutical compositions with wound healing effect.

When other combinations of RNA nucleotide sequences are used in this combinatorial synthesis, a powerful stimulation of tissue regeneration in animals is observed, and similar combinatorial mixtures can accordingly be used in cosmetology as anti-aging creams. Changing the nucleotide sequence of the original modified oligonucleotide also allows the creation of new herbicides and pesticides, as well as acaricides, due to the ability to selectively block certain genes and protein synthesis in fast-growing cells.

EXAMPLE 1

Figure 1:
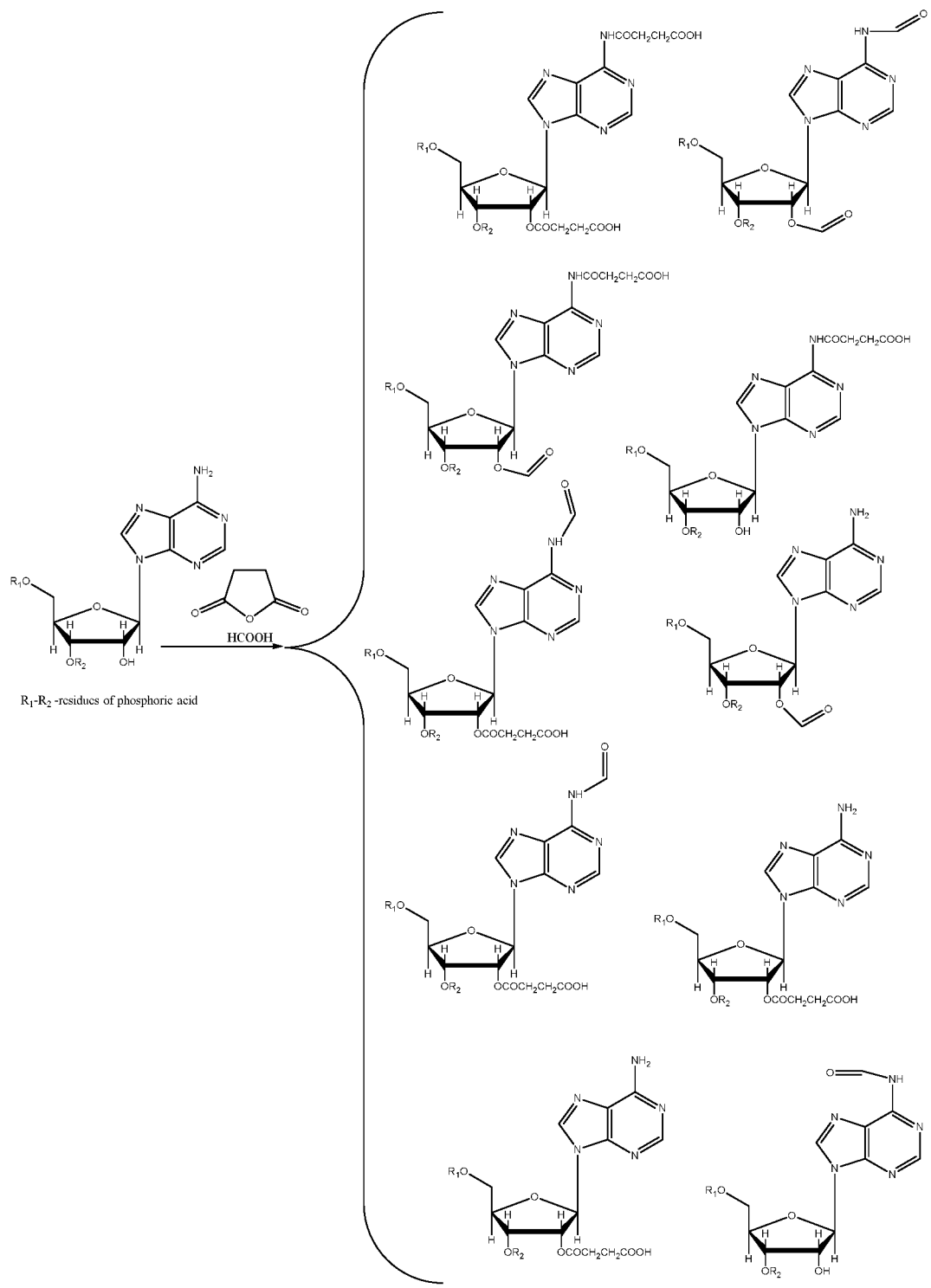
FIG. 1.—The chemical reaction of combinatorial acylation and formylation of the adenosine residue with the formation of the sum of formyl-succinyl derivatives. As a result of this combinatorial modification, 2 adenosine succinyl (substituted by both the amino group and the ribose hydroxyl group) are formed, 2 formyl adenosine (substituted by both the amino group and the ribose hydroxyl group), 2 succinyl-formyl adenosine, 2 monoformyl adenosine (one on the amino group, one on the alcohol), 2 monosuccinyl adenosines (one on the amino group, one on the alcohol). Thus, the double combinatorial modification of only one adenosine in the structure of RNA at the output gives 10 new derivatives. Only this combinatorial mixture has maximum activity and prevents the development of resistance in cancer tumors to chemotherapy drugs. Separately, each derivative of this composition is slightly active and only in the form of a supramolecular system has powerful biological activity.

Obtaining Complementary Derivatives of RNA Oligonucleotides (MATR)

The original 3'-UUGGG-5' sequence is synthesized in a classical way using polynucleotide synthesizers and amplified using a polymerase chain reaction in a modification using RNA-RNA polymerase, which is obvious to a person skilled in the art.

To obtain a complementary RNA oligonucleotide, simultaneous combinatorial synthesis was used with two reagents: succinic anhydride and formic acid.

10 mM 3'-UUGGG-5' is dissolved in 1 ml of dioxane, 20 mM succinic anhydride and 20 mM formic acid are added, the solution is stirred and heated at 30-100 0 C. for 1-60 minutes. The solution was poured into ampoules and lyophilized to remove the solvent and unreacted formic acid. A combinatorial mixture is used in the study of anticancer activity.

One source molecule 3'-UUGGG-5' contains 5 modifiable alcoholic ribose residues and three exocyclic amino groups of guanosine—a total of 8 available groups. Incomplete combinatorial modification with only one modifier—either succinic anhydride or formic acid will yield a combinatorial mixture of 255 derivatives with different degrees of substitution in different positions. The introduction of a second modifier increases the number of derivatives of one oligonucleotide to 380 at the output.

Instead of the 3'-UUGGG-5' sequence, the 3'-UUCCC-5' sequence or either the 3'-UUAAA-5' sequence or any sequence as the starting RNA oligonucleotide of the following nucleotide sequence can be used: 3'-UUN1N2N3-5'; where N1N2N3 correspond to at least one of the following sequences, including a mixture thereof: UUC; UUA; UUG; CUU; CUC; CUA; CUG; AUU; AUC; AUA; AUG; GUU GUC; GUA GUG; UCU; UCC; UCA; UCG; CCU; CCA; CCG; ACU ACC ACA ACG; GCU; GCC; GCA; GCG; UAU; UAC UAA; UAG; GAU; CAC GAA; GAG; AAU; AAC; AAG; GAU; GAC GAA; GAG; UGU; UGC; UGA UGG; CGU; CGC; CGA; CGG; AGU; AGC; AGA; AGG; GGU; GGC; GGA These sequences are recognition triplets of nucleotides in tRNA for each of the known amino acids. A complementary blockade of such/such triplets in the cell will lead to the loss of tRNA ability to attach to the polyribosome and, accordingly, to the loss of protein synthesis.

Calculations of the number of moles of the modifier are carried out according to the combinatorics formulas: $m=4\times(3\times2^{n-1}-1)$; $k=n\times(2^n-1)$, where m is the number of different derivatives of molecules in the combinatorial mixture; n is the number of groups (and moles) available for modification in the oligonucleotide structure (for example, for 3'-UUGGG-5' n=3 guanosine amino groups and 5 hydroxyl groups in the ribose structure, total n=8); k is the number of moles of each modifier modifier (for example, for only one 3'-UUGGG-5' m=764 modifier; k=2040, and the molar ratio is 1:2.67). Thus, having only one oligonucleotide 3'-UUGGG-5' after its modification, we obtain 764 combinatorial complementary derivatives with varying degrees of affinity and hybridizability with the original molecule.

As the result combinatorial mixture (conventional name MATR) is used to study anticancer activity and stimulate tissue regeneration in local application. Derivatives of other oligonucleotides from the above list have pesticidal, herbicidal and acaricidal activities.

Modifiers—succinic anhydride or formic acid can be administered either simultaneously or sequentially—or first inject succinic anhydride, warm the mixture for 30-100 0 C. for 1-60 minutes, and then inject formic acid and also warm the mixture for another 30-100 0 C. 1-60 minutes.

Figure 2:
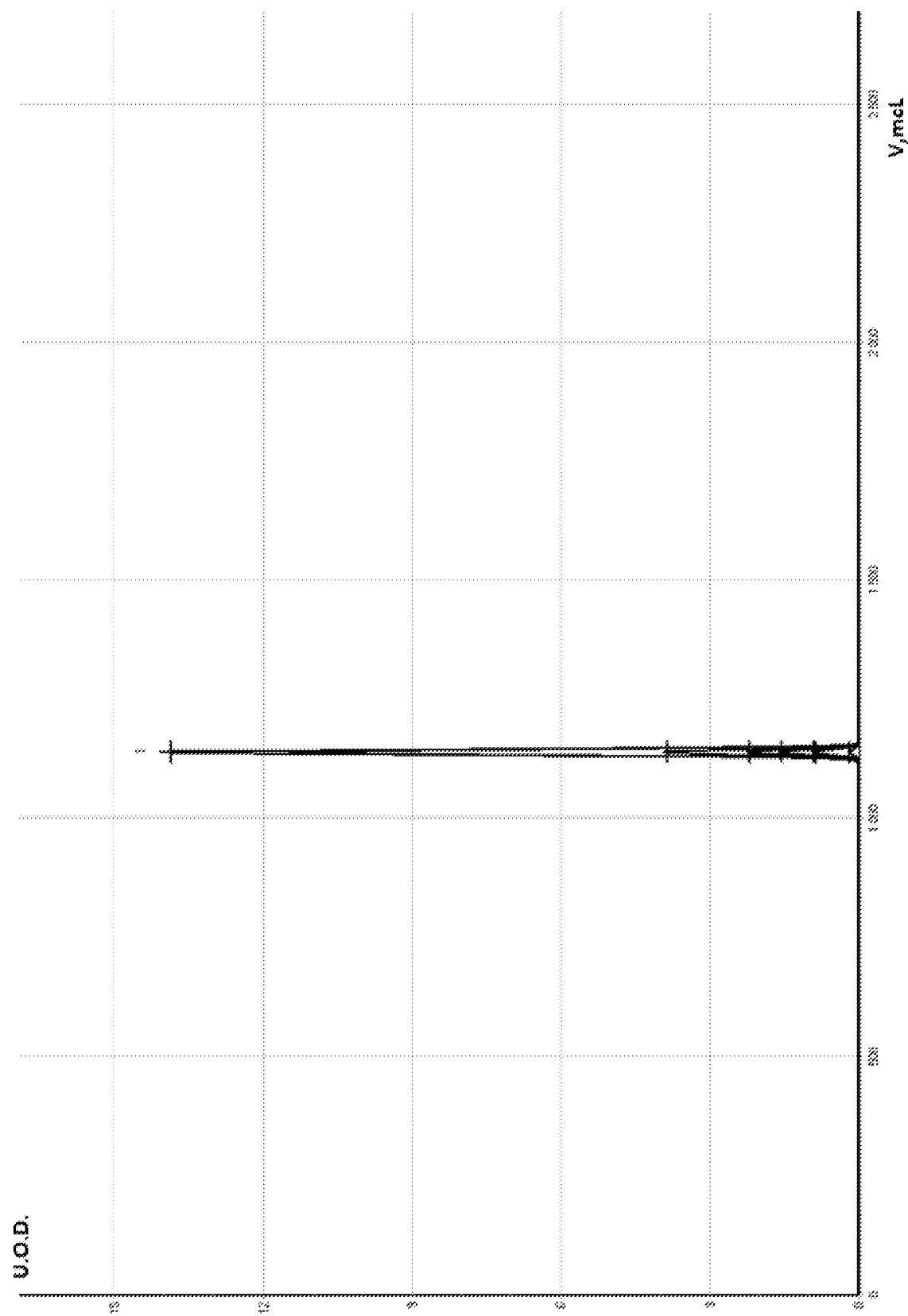
FIG. 2. HPLC of the original 3'-UUGGG-5'oligonucleotide
Figure 3:
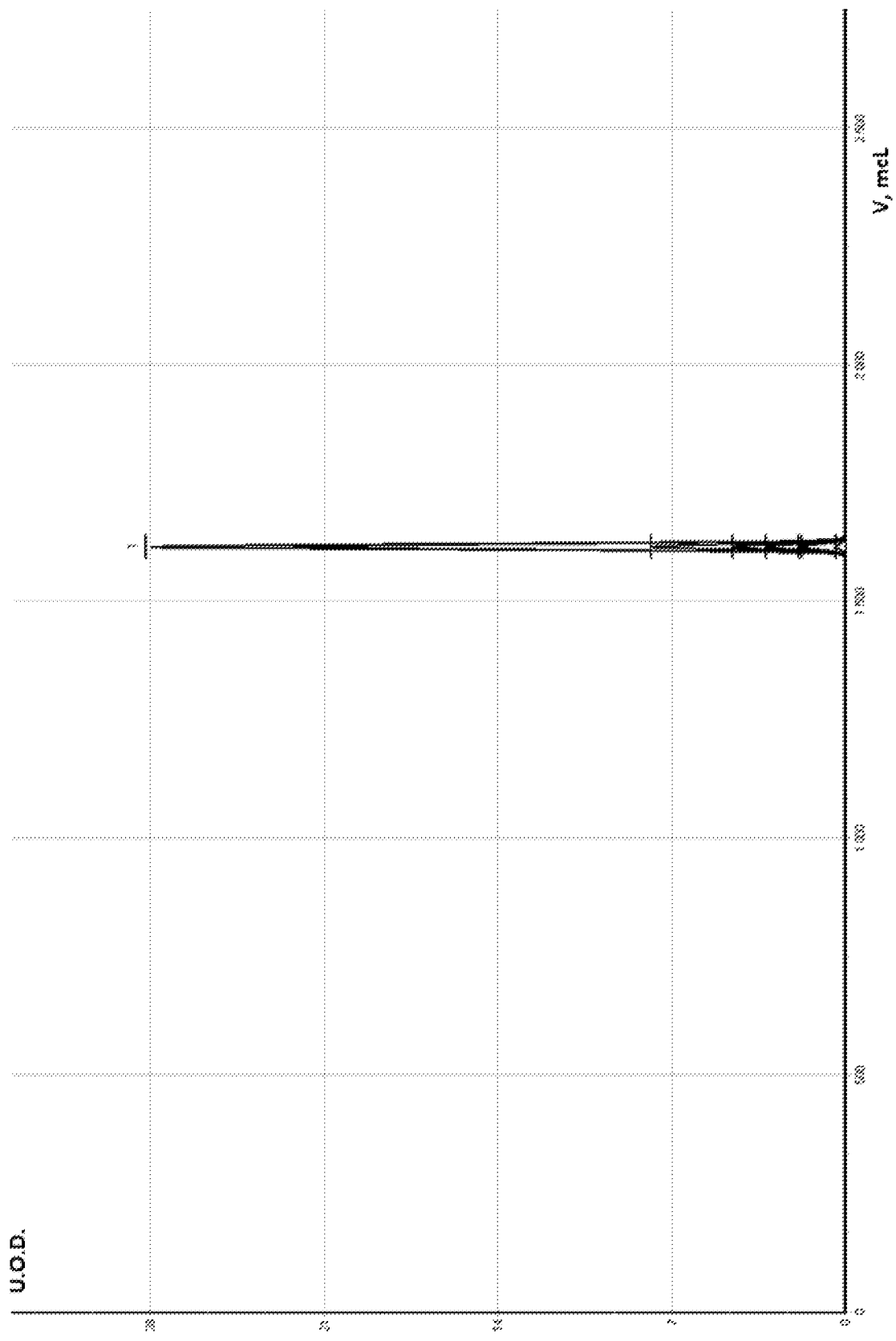
FIG. 3. HPLC completely succinylated on 8 available groups of oligonucleotide 3'-UUGGG-5' (Monitoring the complete completion of the reaction with an excess of one modifier))
Figure 4:
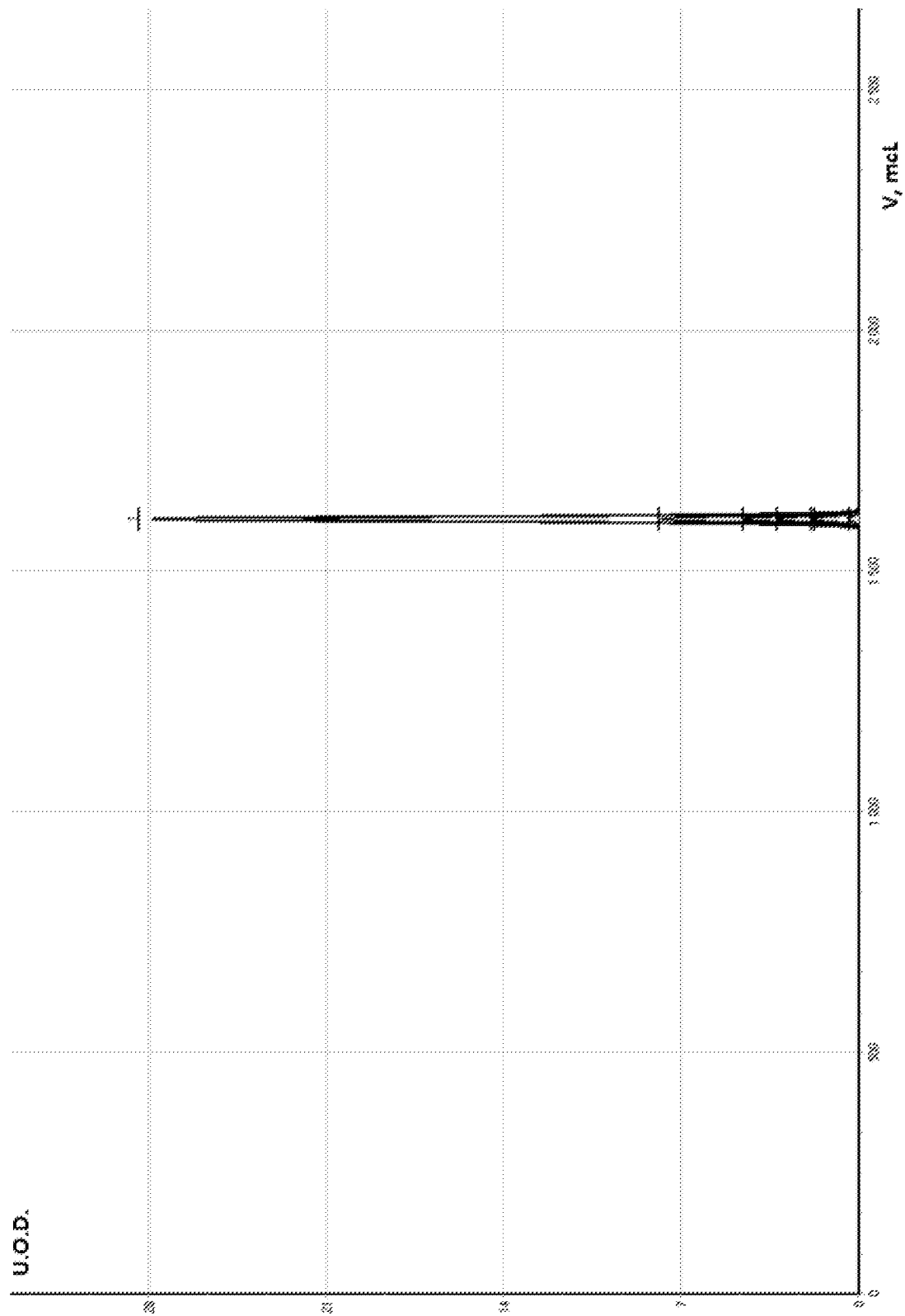
FIG. 4. HPLC of a fully carboxymethylated oligonucleotide 3'-UUGGG-5' according to 8 available groups (Monitoring the complete completion of the reaction with an excess of one modifier)
Figure 5:
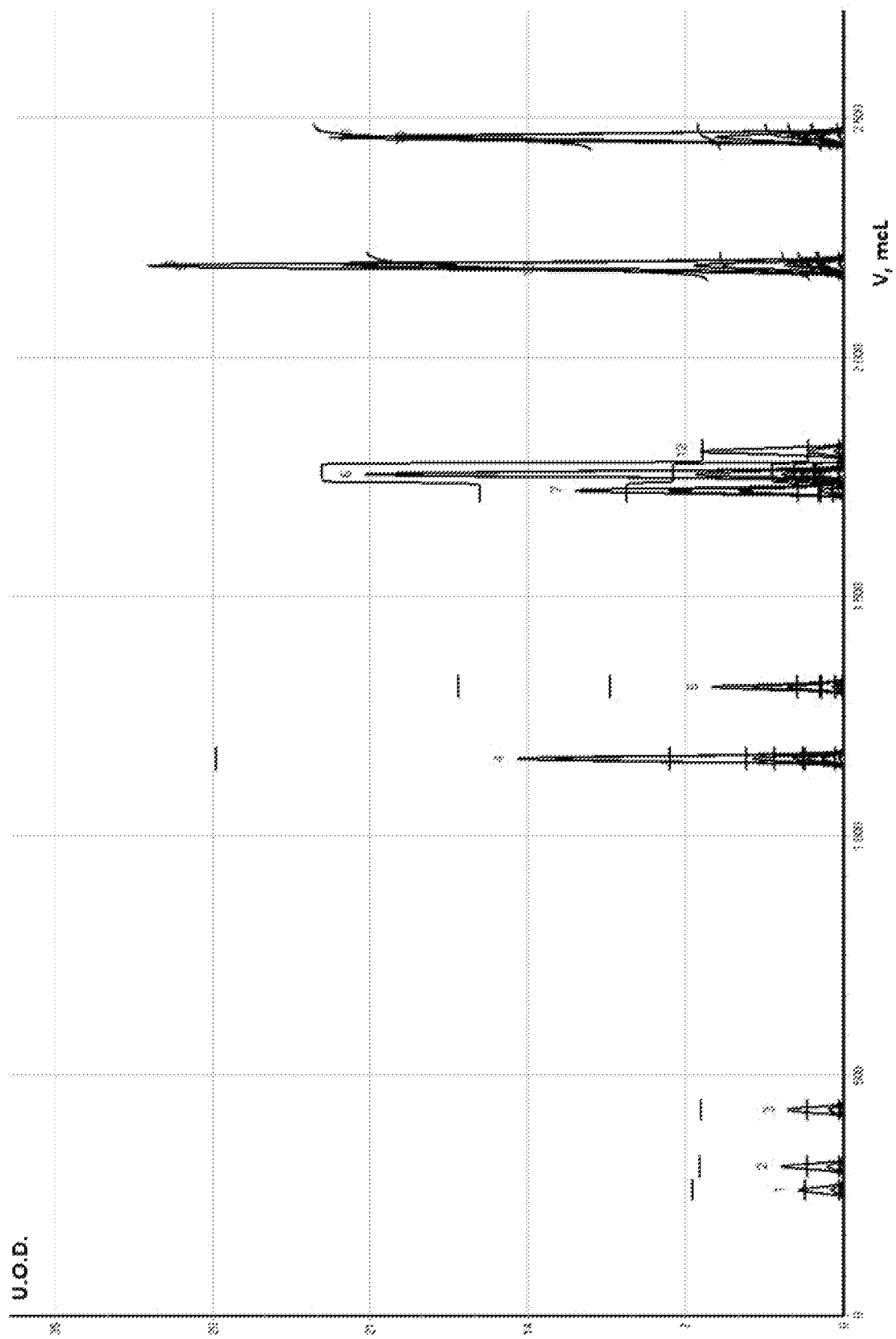
FIG. 5. HPLC after double combinatorial incomplete modification of the 3'-UUGGG-5' oligonucleotide by simultaneous succinylation and formylation

FIG. 2 shows a chromatogram of an unmodified oligonucleotide of structure 3'-UUGGG-5'. FIGS. 3 and 4 show the HPLC chromatograms of two derivatives: a fully succinylated and a fully formulated nucleotide. As can be seen from the graphs, the retention time (volume) of the derivatives differs both from the initial oligonucleotide and among themselves.

This indicates the completion of the acylation and formylation reaction in the structure of the oligonucleotide. The chromatograms also lack peaks of other derivatives, which excludes the hydrolysis of the oligomer to monomeric fragments or the discovery of the adenine purine heterocycle.

The same way in this reaction, maleic anhydride, aconitic anhydride, glutaric, phthalic anhydride and acetic anhydride can be used as one of the modifiers instead of succinic anhydride.

The same way in this reaction, formic acid ethyl ester, monochloroacetic acid, propiolactone, ethylene oxide and other low molecular weight alkylating agents (methyl chloride, ethyl chloride, propyl chloride) can be used as one of the modifiers.

In a similar fashion derivatives of 3'-UUGGG-5 with different ratios of modifiers (succinic anhydride and formic acid) were synthesized and their biological activity was screened for three types of cancer: Lewis carcinoma (CL), Ehrlich ascites cancer (ARE) and HeLa-2 (CL) in vitro.

Table 1 shows the results of biological screening of derivatives.

The calculations were performed using the kumayashi blue mortal dye, the percentage of cell death was determined spectrophotometrically by staining of dead cells against the controls (living culture and completely dead). The accuracy of the spectrophotometer is 3%. The results were processed using the chi-square method for n=5 (5 wells in a plate). The statistical hypothesis of a significant difference in the efficiency of the structure with the maximum number of different derivatives (No. 17 or MATP) from other derivatives obtained empirically was confirmed ($P\leq0.05$).

TABLE 1

Anticancer activity of supramolecular combinatorial derivatives of oligonucleotide 3'-UUGGG-5, wich obtained in the reaction with different molar ratio of modifiers

| No П/П | The molar ratio of reagents * | | | % cell death ** | | |
|---|---|---|---|---|---|---|
| | m | k1 | k2 | CL | ARE | CL |
| 1 | | 16320 | 1 | 0 | 0 | 0 |
| 2 | 764 | 8160 | 1 | 0 | 0 | 0 |
| 3 | -//- | 4080 | 5 | 0 | 0 | 0 |
| 4 | -//- | 2040 | 15 | 0 | 0 | 0 |
| 5 | -//- | 1020 | 31 | 0 | 0 | 0 |
| 6 | -//- | 510 | 63 | 15 | 20 | 20 |
| 7 | -//- | 255 | 127 | 20 | 17 | 17 |
| 8 | -//- | 127 | 255 | 25 | 25 | 20 |
| 9 | -//- | 63 | 510 | 0 | 0 | 0 |
| 10 | -//- | 31 | 1020 | 0 | 0 | 0 |
| 11 | -//- | 15 | 2040 | 0 | 0 | 0 |
| 12 | -//- | 5 | 4080 | 0 | 0 | 0 |
| 13 | -//- | 1 | 8160 | 0 | 0 | 0 |
| 14 | -//- | 1 | 16320 | 0 | 0 | 0 |
| 15 | -//- | 8160*** | 8160*** | 15 | 5 | 5 |
| 16 | -//- | 4080 | 4080 | 17 | 19 | 22 |
| 17 (MATR) | -//- | 2040 | 2040 | 99 | 95 | 100 |
| 18 | -//- | 1020 | 1020 | 15 | 25 | 27 |
| 19 | -//- | 510 | 510 | 0 | 0 | 0 |
| 20 | -//- | 255 | 255 | 0 | 0 | 0 |
| 21 | -//- | 127 | 127 | 0 | 0 | 0 |
| 22 | -//- | 63 | 63 | 0 | 0 | 0 |
| 23 | -//- | 31 | 31 | 0 | 0 | 0 |
| 24 | -//- | 15 | 15 | 0 | 0 | 0 |
| 25 | -//- | 5 | 5 | 0 | 0 | 0 |
| 26 | -//- | 1 | 1 | 0 | 0 | 0 |

TABLE 1-continued

Anticancer activity of supramolecular combinatorial derivatives of oligonucleotide 3'-UUGGG-5, wich obtained in the reaction with different molar ratio of modifiers

| | The molar ratio of reagents * | | | % cell death ** | | |
|---|---|---|---|---|---|---|
| No П/П | m | k1 | k2 | CL | ARE | CL |
| 27 | -//- | 16320 | 0 | 0 | 0 | 0 |
| 28 | -//- | 8160 | 0 | 30 | 44 | 18 |
| 29 | -//- | 4080 | 0 | 22 | 25 | 17 |
| 30 | -//- | 2040 | 0 | 20 | 20 | 15 |
| 31 | -//- | 1020 | 0 | 0 | 0 | 0 |
| 32 | -//- | 510 | 0 | 0 | 0 | 0 |
| 33 | -//- | 255 | 0 | 0 | 0 | 0 |
| 34 | -//- | 127 | 0 | 0 | 0 | 0 |
| 35 | -//- | 63 | 0 | 0 | 0 | 0 |
| 36 | -//- | 31 | 0 | 0 | 0 | 0 |
| 37 | -//- | 15 | 0 | 0 | 0 | 0 |
| 38 | -//- | 5 | 0 | 0 | 0 | 0 |
| 39 | -//- | 1 | 0 | 0 | 0 | 0 |
| 40 | -//- | 0 | 16320 | 0 | 0 | 0 |
| 41 | -//- | 0 | 8160 | 15 | 25 | 17 |
| 42 | -//- | 0 | 4080 | 30 | 25 | 27 |
| 43 | -//- | 0 | 2040 | 0 | 0 | 0 |
| 44 | -//- | 0 | 1020 | 0 | 0 | 0 |
| 45 | -//- | 0 | 510 | 0 | 0 | 0 |
| 46 | -//- | 0 | 255 | 0 | 0 | 0 |
| 47 | -//- | 0 | 127 | 0 | 0 | 0 |
| 48 | -//- | 0 | 63 | 0 | 0 | 0 |
| 49 | -//- | 0 | 31 | 0 | 0 | 0 |
| 50 | -//- | 0 | 15 | 0 | 0 | 0 |
| 51 | -//- | 0 | 5 | 0 | 0 | 0 |
| 52 | -//- | 0 | 1 | 0 | 0 | 0 |

\* m is the number of moles of the 3'-UUGGG-5 oligonucleotide in the combinatorial synthesis reaction; K1 is the number of moles of succinic an-hydride in the reaction; K2 is the number of moles of formic acid in the reaction;
\*\* % cell death in culture after 24 incubations in the presence of a test substance added in a pre-selected concentration (ED90 = 0.2 µg/ml);
\*\*\*the maximum molar ratio at which all groups in the oligonucleotide are replaced, an excess of this ratio leads to the fact that unreacted modifiers remain in the reaction medium-succinic anhydride and formic acid.
As can be seen from table 1, only one derivative No. 17 (MATR) showed an anticancer effect at the level of 95-100% cytotoxic effect on all three types of cancer cell cultures, while other molar ratios of reagents, incl. mono-modified derivative did not possess sufficient cytotoxic activity against cancer cells.

EXAMPLE 2

Synthesis of Succinylated Adenine (Control of Succinylation Reaction)

The 10 mM adenine, 10 mM succinic anhydride are dissolved in 1 ml of dioxane and heated under reflux for 1-60 minutes. Then a vacuum pump is attached to the flask and dioxane is distilled off. The precipitate was recrystallized from dioxane: glacial acetic acid. m.p=163-165 0 C. The spectrum completely confirms the structure of succinyladenine. At the same time, instead of succinic anhydride the maleic anhydride, aconitic anhydride, glutaric, phthalic anhydride and acetic anhydride can be used.

NMR H1: m 2.4-2.7 (—CH2-); m 4.2-6.0 (—CHOH—); d 8.35; 8.63 (—CH—); s 10.60 (—NH—); s 12.2 (—COOH); s 13.82 (—COOH) Elemental analysis (based on derivatogram data): C, 45.1; H, 3.9; N, 10.98; O, 40.09

EXAMPLE 3

Synthesis of Formylated Adenine (Control the Reaction of the Formylation)

The 10 mM adenine, 40 mM formic acid are dissolved in 1 ml of dioxane and heated under reflux in a water bath for 45 minutes. Then a vacuum pump is connected to the flask and dioxane and excess formic acid are distilled off. The precipitate was recrystallized from dioxane: formic acid. m.p=113-115 0 C.

The 1H NMR spectrum completely confirms the structure of formyladenine. At the same time, formic acid ethyl ester, monochloroacetic acid, propiolactone, ethylene oxide can be used instead of formic acid.

NMR H1: d 4.22-4.40 (—CHOH—); s 8.35 (=CH—); s 8.19; 8.63 (=CH—); s 10.51 (—NH—); s 8.59 (—COH); s 8.10 (—COH) Elemental analysis (according to the derivatogram): C, 42.70; H, 3.61; N, 22.66; O, July 31

EXAMPLE 4

Anticancer Activity of MATR

Determination of the anticancer activity of MATR in the cell culture was performed in a HeLa-2 cell culture. The different amount of MATR from 2 to 12 µg/ml of medium was added to medium 199. (see table 1). For the control a culture was without MATR. Cell cultures were monitored for 5 days with daily viewing. The minimum active dose (MAD) of MATR was considered to be its minimum amount, which caused degeneration of 90-95% of the cells (Table 2)

TABLE 2

Comparative characteristics of the sensitivity of the culture of HeLa-2 tumor cells relative to MATR.

| | MAD in | The activity of MATR with different acidity of the medium 199 [1] cell culture. | |
|---|---|---|---|
| Composition | mcg/ml | Control | Experience |
| MATR | 10 | 0 | ++++ |
| Taxotere | 10 | 0 | ++ |
| Normal Saline | — | 0 | 0 |

[1] Cytopathic effect; ++++ degeneration of 100% of cells; 0 lack of degeneration.
When establishing the minimum concentration of MATR, which inhibits cell growth, a comparison was made of the number of cells that survived and the concentration of MATR in solution.

TABLE 3

The effect of MATR on HeLa cells

| Dosage, mcg/ml | The number of cells before incubation, mln | The number of living cells after incubation, mln □ 1000 | | Количествоживыхклеток послеинкубации | |
|---|---|---|---|---|---|
| | | MATP | такcoтер | MATP | Такcoтep |
| 2 | 150000□1000 | 72000 | 155000 | 48 | 100 |
| 4 | 152000□1000 | 21500 | 150000 | 14 | 98 |
| 6 | 150000□1200 | 9900 | 145000 | 7 | 97 |
| 8 | 151000□1000 | 0 | 135000 | 0 | 89 |
| 10 | 160000□1000 | 0 | 130000 | 0 | 82 |
| 12 | 163000□1000 | 0 | 153000 | 0 | 94 |

As can be seen from table 3, the efficient dose of MATR is in the range between 8-12 µg/ml of solution. MATR led to 95% degeneration of tumor cells. To confirm the in vivo antitumor effect, MATR was studied on a model of Ehrlich ascites adenocarcinoma.

EXAMPLE 5

The Study of the Antitumor Effect of MATR on Ascitic Erlich Tumor Adenocarcinoma The antitumor effect of the compositions was studied on Ehrlich ascites carcinoma models in young non-bred mice of both sexes weighing 15-17 g (68 pieces), which were kept on the diet as per vivarium protocol. The 45 mice being inoculated in the liver ascitic fluid from mouse with adenocarcinoma by using insulin syringe 0.1 ml. After 7 days, 42 mice showed signs of a tumor (increased body weight and size of the abdomen), 2 mice died on the second day, 1 mouse showed no signs of a tumor. MATR was injected into ten mice (see Table 4). Additionally, MATR was injected into another 10 mice, and 0.9% sodium chloride solution was injected to ten more mice.

TABLE 4

Quantitative biological and statistical characteristics in the study of antitumor activity of MATR.

| Composition | The term of death of animals after the first injection. Mean value (Days) | |
| --- | --- | --- |
| | Investigational animals | Control Animals |
| MATR | 47.4□1.3 | 3.0□0.5 |
| Taxotere | 15□1.0 | 3□0.5 |

Note:
n = 10, p ≤ 0.05.

MATR was administered to those mice in which blood was drawn originally. Mice with Ehrlich adenocarcinoma after tumor inoculation and treatment by MATR lived 47 days, which is 12 times longer than in the control. With a reliability of more than 99.5%, a significant increase in the anti-cancer activity of MATR against control, taxotere, can be stated. After animal anatomy, it was found that, on average, the number of metastases was 70% less in animals treated with MATR and the average weight of metastases was 20% of the control (taxotere).

EXAMPLE 6

Antitumor Activity of MATR on the Example of Shvets Leukemia

The compositions (MATR and Taxotere) were administered intraperitoneally three times with an interval of two hours in 0.5 ml. For MATR injection aqueous solution was used. The total doses of the compositions were 34.0, 68.0, 84.0, 102.0 and 136 mg/kg. The number of dead animals in each group was confirmed every 24-48 hours. The calculation of the toxic dose, LD50, was carried out according to the protocol. The lethal dose, $LD_{1000}$, was determined experimentally.

As a result of the experiments, it was found that for the MATR compound LD50=3100 µg/kg, LD100=4200 µg/kg. From a comparison of these values, it follows that the toxicity of the aqueous MATR is significantly lower than that of the taxotere control compound (120 mg/kg).

According to histological studies, the death of animals receiving toxic doses of drugs is due to enterotoxicity. There is a pronounced dysplasia of epithelial cells in the intestine, a violation of its regenerative function, a reduction in the number of mitoses. Minor changes were noted in the kidneys: small swelling of the stroma, granular dystrophy of the tubules, small focal hemorrhages.

The antitumor activity of MATR was evaluated from experiments conducted on five groups of animals (10 animals in each group). Outbred white rats weighing 150-200 g under the thigh skin were transplanted 2. 108–2×1010 cells of the inoculating strain of Schwez leukemia. Animals of group 1 served as a control, group II received taxotere, III—taxotere+MATR, IV—MATR in solution, V—MATR in suspension with TWIN-80. The drugs were administered intraperitoneal three times on 4-6 days after tumor transplantation, i.e. during the period of the logarithmic phase of its growth, the second and third times—with intervals of 24-48 hours, respectively. The total dose of drugs was 27.3 mg/kg per pure drug.

Antitumor activity was evaluated by the following physiological parameters:

by tumor volume, v ($cm^3$);

by the degree of inhibition of tumor growth (T/C, %);

survival of animals on the 10th day (SA, %);

the life expectancy of animals (LEA, days).

The calculations were performed according to the following formulas:

$$v = \frac{4}{3}\pi R^3; R = \frac{m_1 + m_2 + m_3}{23}$$

where m 1, m 2, m 3 are three mutually perpendicular measurements of the tumor node;

$$T/C = \frac{V_{contr} - V_{exp}}{V_{contr}}$$

где $V_{кон}$ и $V_{оп}$ - объем опухоли в контрольной и опытной группах соответственно where $V_{contr}$ and Vexp—tumor volume in the control and experimental groups, respectively:

$$SA = \frac{A * 100}{N}$$

Where A is the number of animals on the 10th day after tumor transplantation,

N is the number of animals in this group.

The life expectancy of animals was determined by the number of days elapsed from the moment of tumor inoculation to the death of the last animal in this group. Data on the biological activity of MATR given in table 5.

The analysis of the data presented in table 5 shows that the MATR preparation in its pure form (suspension), compared with the control, inhibits tumor growth by 94%. Its use allows to obtain 100% survival of animals. MATR aqueous solution inhibits tumor growth by 95%, provides 100% survival of animals.

At the same time, their life expectancy is increased by 7-8 days compared to control.

A comparative analysis of the data given in the table allows us to conclude that the claimed compound, MATR in suspension, is more toxic than the preparation MATR in the aqueous solution. In terms of antitumor activity and survival, it is not inferior to the MATR compound in a true solution, but in terms of such an indicator as life expectancy, it significantly exceeds it, since it doubles life expectancy.

TABLE 5

Anticancer efficacy of MATR in different forms-aqueous solution and concentrated suspension

| Name of indicators | Group of animals | | | | |
|---|---|---|---|---|---|
| | 1 (the control) | 2 (MATR suspension) | 3 (MATR aqueous solution) | 4 (mixture of taxotere and MATR) | 5 (taxotere only) |
| The injected dose, mg/kg | | | | 9.1*3 = 27.3 | |
| Toxic dose, LD$_{50}$, mcg/kg | | 3100 | 1500 | 130 | 120 |
| Lethal dose, LD$_{100}$, mcg/kg | | 4200 | 2700 | 180 | 180 |
| Tumor volume, cm3 | 15.0 ± 0.75 | 1.00 ± 0.05 | 0.60 ± 0.03 | 0.75 ± 0.03 | 0.73 ± 0.03 |
| The degree of tumor growth inhibition, T/C,% | 0 | 94 | | 95 | |
| Survival, % | 0 | | | 100 | |
| Life expectancy, days | 14.6 ± 0.5 | 11.6 ± 1.0 | | 21.0 ± 1.0 | |

Therefore, discovering MATR led to the production of a substance more effective than the known antitumor drugs, since the proposed drug is superior to or comparable with known substances in terms of physiological activity characterizing its antitumor effect and compares favorably with them due to the reduction of toxicity.

A number of new properties of MATR were revealed: a high degree of inhibition of tumor growth, significant survival of animals and an increase in their life expectancy while reducing toxicity, which suggests its promise for creating drugs effective in the treatment of malignant tumors.

EXAMPLE 7

Wound Healing Activity

Determination of the effect of the compositions MATR (combinatorial derivative of 3'-UUGGG-5') (D1) and MATR2 (combinatorial derivative of 3'-UUGAA-5') (D2) on tissue regeneration.

The study of the wound healing properties of the compositions was carried out on male Vistar white rats. In 38 animals that were anesthetized with diethyl ether for 2-4 min., A 2 by 2 cm skin area was cut out on the dorsal side of the body, behind the right shoulder blade. The skin was taken with tweezers, it was pulled back, the skin fragment was cut 2 cm in size, wound depth 2 mm, the average area of the wound was 4±1.0 cm$^2$.

The resulting wounds of a polygonal shape were intensively bleeding. Then the wounds of animals first and second groups (10 in each), D1 and D2 compositions were applied. The wounds of rats of the 3rd group were treated with Dexpanthenol (DP), the 4th group of 8 animals was the control group, the wounds of these animals were not treated. The compositions in contact with blood formed a gel form, it was covering entire surface of the wound and capture a small fragment of surrounding skin around the wound.

The glue BF-6 was applied on top of the gel, dried and the animals were released into cells.

The planimetric studies of the wounds were carried out from 1$^{st}$ day of experiment on the 3rd, 6$^{th}$, 9$^{th}$, 11$^{th}$, and 13$^{th}$ days, which made it possible to judge the features of reparative processes.

The measurement of the area of the wounds was carried out as follows: on the celluloid film which was covering the wound entirely, contours were applied, after which the area of the wound surface was determined using graph paper.

Stimulation of the growth of pluripotent hematopoietic cells CD34+

The drugs were studied in an experiment on a model of cytostatic hemo-immunosuppression.

The experiments were performed on 90 male Wistar rats weighing 160-200 g. Animals were kept with free access to water and food. Two experimental and control groups comprised 30 animals each. In both groups, hemo-immunosuppression was induced five times, at 24-hour intervals, by intraperitoneal administration of cyclophosphamide at a dose of 10 mg/kg, rubomycin 2 mm/kg, and prednisone 2 mg/kg in 3 ml of normal saline.

On the next day after the end of the administration of hemoimmunosuppressive drugs, the animals of the experimental group were smeared the skin at the withers with one of the gels in an amount of 0.5 g/animal and BF6 glue was applied. The gel was changed every other day. Animals of the control group at the same time were followed same protocol but applied to the skin with a placebo—carbopol gel without active substances. The effect of the drug was evaluated based on blood test results on 1, 10, 30, 60, 90 days of the experiment.

The proliferative activity of CD34+ stem cells was studied using the CD34 Count kit [2] for cytofluorimetry using a FACS Calibur flow cytofluorimeter. Digital material was processed using nonparametric statistics with the definition of the criterion "U" according to Wilcoxon-Mann-Whitney.

The results of the first series of experiments on the study of wound healing properties (Table 6) showed that wound healing at all stages of the study was significantly accelerated under the influence of compositions D1 and D2. The effectiveness of composition D1 was statistically higher than that of composition D2 and DP.

TABLE 6

Indicators of healing of skin wounds in rats under the influence of compositions D1 and D2

| Composition | n | Wound Area * (S) during the observation, cm2 (M ± m) | | | | |
|---|---|---|---|---|---|---|
| | | 1-3 days | 3-6 days | 6-9 days | 9-11 days | 11-13 days |
| D1 | 10 | 4.0 ± 0.7 | 1.1 ± 0.4 | 0.2 ± 0.1 | — | — |
| D2 | 10 | 4.2 ± 0.9 | 2.0 ± 0.4 | 0.7 ± 0.2 | 0.4 ± 0.1 | — |
| DP | 10 | 4.1 ± 1.0 | 3.2 ± 0.3 | 2.4 ± 0.3 | 1.0 ± 0.3 | 0.3 ± 0.1 |
| Control | 8 | 4.0 ± 0.6 | 3.6 ± 0.6 | 2.6 ± 0.6 | 1.5 ± 0.5 | 0.5 ± 0.2 |

* P ≤ 0.05As can be seen from table 6, the wounds that treated by D1 composition were healed 2 times faster (days 13 to 6$^{th}$ day) of control sample DP, wich efficiency close to control value.

Wound epithelization was initiated on the second day after application of the composition.

An interesting fact is noted the difference between options D1 and D2, although they are identical based on content of composition.

Table 7 shows the results of a study of the effect of the compositions on the number of pluripotent CD34+ cells in rat blood. The normal level of CD34 cells in the blood ranges from 3 to 6*10$^6$ cells/liter.

TABLE 7

The number of pluripotent cells CD34 + in the blood of rats under the influence of compositions D1 and D2

| | | CD34 + * $10^6$ cells/l | | | | |
|---|---|---|---|---|---|---|
| Composition | n | 1 days | 10 days | 30 days | 60 days | 90 days |
| D1 | 30 | 1.2 ± 0.4 | 4.4 ± 0.6 | 12.3 ± 0.8 | 15.2 ± 0.9 | 15.6 ± 1.0 |
| D2 | 30 | 1.0 ± 0.3 | 4.3 ± 0.7 | 12.0 ± 0.7 | 14.3 ± 0.8 | 15.0 ± 1.1 |
| Carbopol ** | 30 | 1.7 ± 0.3 | 1.0 ± 0.2 | 1.9 ± 0.2 | 4.2 ± 0.3 | 4.0 ± 0.4 |

* $p \leq 0.05$
** The average in the control group without immunodeficiency was 4.2 ± 0.3

The introduction of cytotoxic drugs led to a decrease in the level of CD34 at the time of initiation of therapy by 3-4 times, compared with the initial level. Moreover, the animals of both groups were able to restore them to normal values. However, bone marrow regeneration processes with the restoration of peripheral blood indices proceeded in different ways.

Local application of samples of D1 and D2 to the skin of rats accelerated these processes by about 2 times, as evidenced by the excess of blood parameters of animals of the experimental group by 30 days more than 2 times, while these indicators in animals of the control group came to normal values only on the 60th day.

The increase in the number of pluripotent cells, which correlated with the acceleration of wound regeneration, indicates a predominant stimulation of stem cell division at the periphery, rather than an increase in bone marrow functions. The maximum effect from the use of D1/D2 was observed on the 60th day, and the restoration of the physiological level of pluripotent cells was observed already on the 10th day after the start of application of the gel. Due to the fact that the gel was applied to intact skin, we can talk about the high resorptive properties of the gel and its general effect on the whole body.

Therefore, the action of D1/D2 leads to selective stimulation of division of pluripotent cells in the wound and stimulation of excretion of fibroblast growth factors, contribute to a 6-fold acceleration of restoration of animal immunity after induced immunodeficiency.

Also, variants of the compositions in the form of gel D1 and D2 have a significant regenerative ability to wounds, accelerating epithelization and wound healing on average twice.

Gels D1 and D2 have the ability to be absorbed through the skin and have a beneficial effect on the immune system of the whole organism through stimulation of the division of pluripotent cells CD34.

EXAMPLE 8

Acaricidal Activity

Ovicidal test on a spider mite (*Tetranychus urticae*) by immersion using a combinatorial mixture of MATR based on oligonucleotide 3'-UU UAA-5'.

Four adult female spider mites (*Tetranychus urticae*), which are a sensitive species, were placed on each 15 mm leaf disc cut from young leaves. After laying the eggs for 24 hours at 26-28° C., the females were removed and the eggs laid on the discs were calculated.

The treatment was carried out by immersing the disks in solutions containing the corresponding concentration of active compounds (using DMSO as a co-solvent in an amount of no more than 5% in the test solution). The dive lasted 5 s.

After processing, the disks were dried on dry filter paper, then stored on wet filter paper at 26-28° C. in a Petri dish until they were removed from untreated control eggs, and then the excretion coefficient was determined. Each experiment was repeated four times using at least three similar experiments for each concentration.

The values of efficacy given for each concentration show the average value of treatments carried out on at least 250 tick eggs. Corrected mortality was calculated according to Abbott. The results expressed in percentages, are shown in table. 8.

TABLE 8

The survival rate of spider mite eggs after processing developed by the combinatorial MATR library

| | % surviving eggs | | | | |
|---|---|---|---|---|---|
| Sample | 1 | 2 | 3 | 4 | 5 |
| Experience, MATR | 11 ± 2 | 5 ± 1 | 12 ± 2 | 8 ± 1 | 17 ± 3 |
| The control | 67 ± 8 | 72 ± 9 | 60 ± 9 | 64 ± 10 | 53 ± 9 |

$P < 0.01$

As can be seen from the table, the processing of the MATR solution with samples, leads to a significant decrease in the survival rate, which indicates the presence of acaricidal action of the combinatorial MATR library based on 3'-UUUAA-5' oligonucleotide

EXAMPLE 9

Herbicidal Activity

Plastic trays were lined with plastic wrap and filled with pasteurized sandy loamy soil Sassafras (pH 6.5, 1% O.M.). One tray was seeded with wheat (*Triticum acstivum*), barley (*Hordeum vulgare*), wild oats (*Avena fatua*), roofing bonfire (*Bromus Secalinus*), leaf-tailed mouse-tail (*Alopecurus myosurocdes*), bluegrass annual (*Poa annua*), Italian bristle, setaria by tares (*Liolium multiflorum*), and rapeseed (*Brassica napus*).

The second tray was inoculated with the following plants: Matricaria inodora, tenure (*Gallum aparine*), Russian solyanka (*Salsola kali*), shepherd's purse (*Capsella bursapastoria*), Cochia (*Cochia scoparia*), black nightshade (*Solarium. Nigrum*), Veronica (*Veronica persica*), highlander climbing (*Polyconum convolvulus*) and sugar beet (*Beta vulgaris*). For post-emergence treatment, the first tray or tray was seeded 14 days before spraying, and the second tray was planted 24 days before treatment.

Plants after post-emergence treatments were classified by height from 1 to 15 cm, depending on the species. Wheat, barley and oatmeal were in the developmental stage of 2 leaves (Stage II Ladors). Before spraying for pre-emergence treatments, another set of trays was prepared identically. Herbicides were diluted in a non-phytotoxic solvent and applied to trays using a belt sprayer.

Additionally, three other species were evaluated: *Veronica hederae folla*, starfish (*Stellaria media*) and *Viola arveusis*. These plants were grown in five-inch pots containing the same soil as previously described. Plants were grown for 22 days prior to treatment. The application of the herbicide was carried out in the same way as when screening trays. Plants were grown in a greenhouse for 21 days, during which time a visual assessment was made when compared with the untreated control. The assessment was based on a scale from 0—no effect to 100—complete death. The results are shown in table. 9-11.

TABLE 9

Herbicidal action of the proposed method MATR.

| Consumption rate (g/ha) | 7.9 | 4 | 2 |
|---|---|---|---|
| Before germination | | | |
| Wheat | 0 | 0 | 0 |
| Barley | 0 | 0 | 0 |
| Sugar beet | 50 | 1 | 20 |
| Rape | 10 | 0 | 0 |
| Wild oats | 0 | 0 | 0 |
| Bonfire | 0 | 0 | 0 |
| Roofing | 0 | 0 | 0 |
| Foxtail mouse-tail | 0 | 0 | 0 |
| Bluegrass annual | 0 | 0 | 0 |
| Bristle green | 0 | 0 | 0 |
| Italian chaff | 0 | 0 | 0 |
| Mauetarla Inodora | 0 | 0 | 0 |
| Galium aparine | 0 | 0 | 0 |
| Russian solyanka | 0 | 0 | 0 |
| Shepherd's bag ordinary | 20 | 10 | 0 |
| Cochia | 0 | 0 | 0 |
| Black nightshade | 0 | 0 | 0 |
| Crowberry | 0 | 0 | 0 |
| Highlander climbing | 0 | 0 | 0 |
| After germination | | | |
| Wheat | 0 | 0 | 0 |
| Barley | 0 | 0 | 0 |
| Sugar beet | 80 | 90 | 90 |
| Rape | 90 | 80 | 90 |
| Wild oats | 0 | 0 | 0 |
| Bonfire | 0 | 0 | 0 |
| Roofing Foxtail | 0 | 0 | 0 |
| mouse-tail | 0 | 0 | 0 |
| Bristle green | 0 | 0 | 0 |
| Italian chaff | 0 | 0 | 0 |
| Matrecarta Inodore | 70 | 60 | 50 |
| Galium aparire | 0 | 0 | 0 |
| Russian solyanka | 90 | 90 | 70 |
| Shepherd's bag ordinary. | 90 | 90 | 80 |
| Kopia | 80 | 70 | 50 |
| Black nightshade | 60 | 60 | 50 |
| Veronica | 50 | 30 | 30 |
| Highlander climbing | 70 | 30 | 0 |
| Veronica hederaefolla | 0 | 0 | 0 |
| Viola arvensls | 65 | 50 | 0 |
| Stellarla media | 95 | 80 | 75 |
| Before germination | | | |
| Barley (spring) | 0 | 0 | 0 |
| Barley (winter) | 0 | 0 | 0 |
| Black nightshade Foxtail | 30 | 0 | 0 |
| Mouse-tailed | 0 | 0 | 0 |
| Bluegrass annual | 0 | 0 | 0 |
| Cleavers | 0 | 0 | 0 |
| Roofing fire | 0 | 0 | 0 |
| Field Yart | 20 | 0 | 0 |
| Viola arvensis | 0 | 0 | 0 |
| Bristle green | 0 | 0 | 0 |
| Italian chaff | 0 | 0 | 0 |
| Veronica hederaefolla | 0 | 0 | 0 |
| Acgilops cyllndrlca | 0 | 0 | 0 |
| Kochla scoparla | 60 | 60 | 0 |
| Mary White | 70 | 70 | 0 |
| veronica persica | 30 | 30 | 20 |
| Pane | 70 | 40 | 40 |
| Russian solyanka | 70 | 20 | 0 |
| Matricaria Inodora | 0 | 0 | 0 |

TABLE 9-continued

Herbicidal action of the proposed method MATR.

| Consumption rate (g/ha) | 7.9 | 4 | 2 |
|---|---|---|---|
| Sugar beet | 90 | 90 | 40 |
| Wheat (spring) | 0 | 0 | 0 |
| Wheat (winter) | 0 | 0 | 0 |
| Highlander climbing | 10 | 20 | 10 |
| Wild oats | 0 | 0 | 0 |
| Послппоявлениявсходов | | | |
| Barley (spring) | 0 | 0 | 0 |
| Barley (winter) | 0 | 0 | 0 |
| Black nightshade | 30 | 0 | 0 |
| Foxtail Mouse-tail | 20 | 0 | 0 |
| Bluegrass annual | 0 | 0 | 0 |
| Cleavers | 30 | 20 | 0 |
| Roofing fire | 0 | 0 | 0 |
| Field Yart | 90 | 90 | 90 |
| Viola arvensis | 70 | 60 | 60 |
| Bristle green | 0 | 0 | 0 |
| Italian chaff | 0 | 0 | 0 |
| Veronica hederaefolla | 0 | 0 | 0 |
| Aeqllops cyllndrlca | 0 | 0 | 0 |
| Kochla scoparia | 100 | 90 | 00 |
| Mary White | 100 | 100 | 100 |
| Veronica persica | 100 | 60 | 60 |
| Rape | 100 | 100 | 90 |
| Russian solyanka | 100 | 100 | 100 |
| Matricaria Inodora | 100 | 100 | 80 |
| Sugar Soskle | 100 | 100 | 100 |
| Wheat | 0 | 0 | 0 |
| Wheat (winter) | 0 | 0 | 0 |
| Highlander Paved | 70 | 50 | 30 |
| Wild oats | 0 | 0 | 0 |

TABLE 10

Phytotoxic effect of the claimed method MATR

| The dose of the compound about g/ha | % damaged of cultivated plants used as indicators | | |
|---|---|---|---|
| | peas | rape | sugar beet |
| 0 | 0 | 0 | 0 |
| 2.18 | 0 | 5 | 60 |
| 4.37 | 0 | 5 | 25 |
| 8.75 | 0 | 5 | 75 |
| 17.5 | 0 | 40 | 90 |
| 35.0 | 0 | 75 | 100 |
| 35 g/ha (10 days of incubation) | 0 | 10 | 60 |

TABLE 11

Phytotoxic effect of the prototype

| The dose of the compound about g/ha | % to cultivated plants damage used as indicators | | |
|---|---|---|---|
| | ropox | rapeseed | sugar beet |
| 0 | 0 | 0 | 0 |
| 0.5 | 0 | 0 | 20 |
| 1.1 | 0 | 0 | 55 |
| 2.25 | 35 | 60 | 95 |
| 4.5 | 90 | 80 | 100 |
| 9.0 | 100 | 90 | 90 |
| 9 g/ha (incubation for 95 days) | 95 | 70 | 85 |

As can be seen from tables 9-11, the proposed combinatorial MATR library has herbicidal activity on a wide range of weeds, and on cultivated plants has a less pronounced growth-inhibitory effect and can be successfully used as a herbicidal agent.

EXAMPLE 10

Pesticidal Activity

The compounds of the present invention exhibit excellent pesticidal activity against pests such as winged insects, lepidopteran insects, winged insects, dipteran insects, hymenoptera insects, orthoptera insects, winged insects, insects in which only part of the wing is covered with scales, mites and parasites nematode plants.

Among them are the following pests Semi-winged insects bugs (*Heteroptera*), such as bean bugs (*Riptortus clavatus*), southern green bug bugs (*Nezara vindula*), bugs of the *Lygus* sp family, white-winged bugs (*Bhssus leucopterus*) and pear bugs (*Steashi mtis*)), thick-headed (*Circuhfer* sp), such as green rice thick-headed (*Nephotettix cmcticeps*) and thick-headed *Enpoasca* sp *Erythroneura* sp *circuhgfer* sp, delphacids (Delphacidae), such as brown rice delphacid (*Nilaparvata lugens*), white-winged delphacid (*Sogatella furcifera*) and small brown delphacid (*Laodelphax stnatellus*). Among them also jumping plant fleas (Psylhdae), such as leaf fleas (*Psylla* sp), whiteflies (Aleyrodidae), such as potato whiteflies (*Bemisia tabaci*) and greenhouse whiteflies (*Tnaleurodes vaporanorum*), aphids (Aphdidae), such as vinifera flea, (*Myzus persicae*), apple aphid (*Aphis roti*), cotton aphid (*Aphis gossypn*), *Aphis fabae*, false cabbage aphid (*Rhopalosiphum psedodrassicas*), greenhouse potato aphid (*Aulacorthuim solani*) and common aphid (*Schizaphis graminum*), mealybugs or scale insects, such as those of the *Pseudococcus comstocki* family, red wax insects (*Ceroplastes rubens*), California insects (*Comstockaspis perniciosa*) and oriental citrus insects (*Unaspis yanonensis*), lepidoptera insects (Eastern Tortoises, *Tona marasna, magnata*), leafy leaflet of fruit trees (*Adoxphyes orana*), leaflets of the family *Sparganothis pillenana*, oriental leaflet peach (*Graphohtha molesta*), bean grinder (*Legumimvora glycimvorella*), codling moth (*Laspeyresia pomonella*), leafworms of the *Eucosma* sp family and grape leafworm (*Lobesia botrana*), slugs such as grape slug (*Eupocilha ambiquella*, such as psychicidae) bagworms of the species *Bambahna* sp, moths (Tmeidae), such as European grain moth (*Nemapogon granellus*) and clothes moth (*Tinea translucens*), moths of the Lyonetndae family, such as *Lyonetia prumfohella*, variegations, such as apple leaf moth (*Phyllonorycter ngoniello*), Phyllocmstidae, such as citrus moth (*Phyllocnistis cetomellida*), and iponomethoid moths (*Prays citn*) of vitreous moths (*Synanthedon* sp) such as grape moths (*Paranthene regahs*) and *Synanthedon* sp family glass moths, Gelechndae family moths such as pink cotton boxworm (*Pectinophora gossypiella*), potato tuber worm (*Phthonmaea operculella*) and *Stomopteryx* sp, Carposimdae such as peach leaflet (*Carposma mponensis*), slug slugs, slug slugs Eastern (*Monema flavescens*), pyralid moths, such as Rice stem moth (*Chilo suppressahs*), Rice leaf maker (*Cnaphalocrocis medinahs*), European corn moth (*Ostrmia nubilahs*), Eastern corn moth (*Ostrmia furnacahs mollsahs*) large wax moth (*Gallena mellonella*), a small corn moth (*Elasmopalpus hgnosellus*) and a meadow moth (*Loxostege sticticahs*), whites, such as common cabbage white caterpillars (*Piens garay*), geometric moths, such as wormwood moths, *Asocotis selenana*, and caterpillars of the caterpillar species mollusks, such as tobacco cucurbit (*Manduca sexta*), bagworms, such as tea-bear (*Euproctis pseudoconspersa*) and unpaired silkworm (*Lymantna dispar*), dipper, such as the American white butterfly (*Hyphantna cunea*), scoops, such as tobacco scoop (*Hehothis virescens*), cotton scoop (*Hehcoverpa zea*), beet warrior worm (*Spodoptera exigua*), cotton scoop (*Hehcoverpa armigera*), common scoop (*Spodoptera htura*), cabbage warrior worm (*Mamestra brassica*) (*Agrotis ipsilon*), rice war worm (*Pseudaletia separata*) and scoop ni (*Tnchoplusiani*) Nutcrackers (*Conodeus* sp,), such as the nutcracker larvae of the species *Agnotes* sp and *Conodeus* sp, ladybugs, such as the twenty-eight-spotted ladybug (*Epilachna vigmticetopunetata*), and the Mexican ladybug (*Epilachna vanvestis*), black beetles, such as the red-brown rice crustacean (*Tnbukumumane* such as the white-spotted long-legged beetle (*Anoplophora malasiaca*) and the black barbel (*Monochamus alternatus*), seed bugs, such as the bean weevil (*Acanthoscehdes obtectus*) and the radiant bean weevil (*Callosotruchus chmensis*), leaf beetles, such as (leptemata leptemata) (*Diabrotica* sp), rice leaf beetle (*Oulema oryzae*), small beetroot leaf beetle (*Chaetocnema concmna*), mustard beetle (*Phaedon cochleanas*), cereal leaf beetle (*Oulema melanopus*) and leaf beetles of the *Dicladispa armigere* Apionidae family, such as *Apion godmani*, weevils such as rice weevil (*Anthonomus cerephus, Rhondymophus rhymonchophus grandmus, Anthonomus grandis*) (*Sitophilus zeamais*), bark beetles, trogids, bread grinder Diptera insects rice centipede (*Tipra ano*), rice gall midge (*Tanytarsus oryzae*), *Orseoha oryzae, Ceratitis capitata*, rice moth (*Hydrelha gnseola*), *Drosophila* cherry (*Drosophila suzukn*), Swedish fly (*Oscmella frit*), rice stem larva (*Chlorops oryzaeh*) phoebe, phyto bean bean moth (*Linomyza trifoln*), beetroot fly (*Pegomya hyoscyami*), corn larva (*Hylemia platura*), Sorghum fly (*Athengona soccata*), real fly (*Musca domestica*), *Gas-trophilus* sp, flies of the *Stomoxys* sp family, *Aedes aegypti, Culex pipiens, Anopheles slensis,* and *Culex tntaemorhynohus* Hymenoptera insects bread sawflies (*Cephus* sp), eurytomids (*Harmohta* sp.), Cabbage sawfly (*Athaha* sp), hornets (*Vespa* sp) and *Rygerthaurus anthrax* Rameter, American cockroach (*Penplaneta amencana*), bear (*Gryllotapla afncana*), migratory locust (*Locusta migratona migratonodes*), and *Melanoplus sangumipes* Termite insects termites of the species *Reticuhtermes speratus* and *Coptotermes formosanus*. Bubble insects yellow tea tripods (*Scirtothnps dorsahs*), *Trips* of the species *Trips palmi*, greenhouse *Trips* (*Hehothnps haemorrhohdahs*), flower *Trips* (*Frankhmella occidentahs*) and mossy tripe rice (*Harlothnps aculeatus*) Red apple and red clover (red apple) *Tetranychus kanzawai*), red citrus tick (*Panonychus citn*), European red tick (*Panonychus ulmi*), yellow spider mite (*Eotetranychus carpim*), Texas citrus mite (*Phyllocoptruta oleivora*), *Polyhagotarsonemus latus* mite, false spider mites (*Brevipalpus* sp) root quail (*Rhizoglyphus robim*) and mold quail (*Tyrophagus putrescentiae*) nematodes nematodes sp), soybean cyst (*Heterodera glycmes*), white rice nematode (*Aphelenchoides besseyi*) and pine nematode (*Bursaphelenehus xylophilus*). Other pests and parasites of Gastropoda, such as the apple snail (*Pomacea canahculata*), slugs (*Indiana* sp) and *Achatina* (*Achatina fuhca*), woodlice (*Isopoda*), such as isopods and leggy woodlice, lice (*Liposcehs* sp), *Ctenplepisma* sp, Pu, *Tnchodectes* sp, *Cimex* sp, animal parasitic mites such as *Boophilus microplus, Aemaphysahs longicorms* and Epidermoptidae. Further, the MATR of the present invention is also effective against pests that are resistant to organophosphorus compounds, carbamate compounds, synthetic pyrethroid compounds, acylurea derivatives or conventional insecticides. Thus, the compounds of the present invention exhibit excellent pesticidal activity against a wide range of pests, including winged insects, lepidopteran insects, winged insects, dipteran insects, hymenoptera insects, orthoptera insects, orthoptera insects, insects, which have only a part of the wing covered with scales. and parasitic *nematodes* on plants, and are also able to control pests that have become resistant to common pesticides.

Insecticidal Test Against Cabbage Moth:

MATR based on the oligonucleotide 3'-UUAGA-5', diluted with water so that the concentration of the active ingredient was 500 ppm. Cabbage leaves are immersed in the resulting diluted solution, air dried and placed in a polyvinyl chloride cup. Larvae of cabbage moth are released into the cup and the cup is covered with a lid then the cup is placed in a temperature-controlled chamber for 25 days at a temperature of 25° C. and the number of dead insects is counted in order to determine the percentage of mortality. Spend two consecutive experiments. The average mortality rate for this version of MATR was 100%.

Rice Delphacid Insecticide Test

MATR based on the oligonucleotide 3'-UUAGA-5', diluted with water so that the concentration of the active ingredient was 500 ppm. The resulting diluted solution is immersed in the stems and leaves of rice, which are then dried in air and placed in a test tube. 5 larvae of brown rice delphacide are released into the test tube and the opening of the tube is plugged with a porous substance.

Then the test tube for 6 days is placed in a thermostatic chamber with a temperature of 25° C. and count the number of dead insects, in order to determine the percentage of mortality. Spend two consecutive experiments. The average mortality rate for this version of MATR was 100%.

Insecticidal Test Against Radiant Bean Weevil

MATR based on a 3'-UUAGA-5' oligonucleotide is diluted with water so that the concentration of the active ingredient is 100 ppm. with a capacity of 60 ml. Five adult females of radiant bean weevil are released into the cup and the cup is closed with a lid. Then the cup for 4 days is placed in a temperature-controlled chamber with a temperature of 25° C. and count the number of dead insects in order to determine the percentage of mortality. Spend two consecutive experiments.

The average mortality rate for this version of MATR was 100%.

EXAMPLE 11

Pharmaceutical Compositions

Various methods of administering supramolecular combinatorial derivatives of RNA oligonucleotides (MATR) can be used. The MATR composition can be given orally or can be administered by intravascular, subcutaneous, intraperitoneal injection, in the form of an aerosol, by ocular route of administration, into the bladder, topically, and so on. For example, inhalation methods are well known in the art.

The dose of the therapeutic composition will vary widely depending on the particular administered MATR, the nature of the disease (purpose), frequency of administration, route of administration, clearance of the agent used from the host, and the like. The initial dose may be higher with subsequent lower maintenance doses. The dose can be administered with a frequency of once a week or once every two weeks, or divided into smaller doses and administered once or several times a day, twice a week, and so on to maintain an effective dose level.

In many cases, oral administration would require a higher dose than intravenous administration. The compounds of this invention may be included in a variety of compositions for therapeutic administration.

More specifically, the compounds of the present invention can be incorporated into pharmaceutical compositions in combination with suitable pharmaceutically acceptable carriers or diluents and can be incorporated into preparations in solid, semi-solid, liquid or gaseous forms, such as capsules, powders, granules, ointments, creams, foams, solutions, suppositories, injections, forms for inhalation use, gels, microspheres, lotions and aerosols.

Therefore, the administration of the compounds can be carried out in various ways, including oral, buccal, rectal, parenteral, intraperitoneal, intradermal, percutaneous, intratracheal administration and so on.

The MATR can be distributed systemically after administration, or can be localized using an implant or other composition that holds the active dose at the site of implantation. The compounds of the present invention can be administered alone, in combination with each other, or they can be used in combination with other known compounds (for example, classic anti-cancer agents, anti-inflammatory agents, immunomodulators and so on).

In pharmaceutical dosage forms, the compounds may be administered in the form of their pharmaceutically acceptable salts. The following methods and excipients are given by way of example only and are not in any way limiting.

For oral administration, the compounds can be used alone or in combination with suitable additives for the manufacture of tablets, powders, granules or capsules, for example, with conventional additives such as lactose, mannitol, corn starch or potato starch; with binding agents, such as crystalline cellulose, cellulose derivatives, gum arabic, corn starch or gelatins; with disintegrants such as corn starch, potato starch or sodium carboxymethyl cellulose; with mazyvayuschimi agents such as talc or magnesium stearate, and, if desired, with diluents, buffering agents, moistening agents, preservatives and flavoring agents.

The compounds can be incorporated into injectable compositions by dissolving, suspending or emulsifying them in an aqueous or non-aqueous solvent such as vegetable or other similar oils, synthetic aliphatic acid glycerides, esters of higher aliphatic acids or propylene glycol; and, if desired, with conventional additives, such as solubilizers, isotonic agents, suspending agents, emulsifiers, stabilizers and preservatives. The compounds may be used in an aerosol composition for inhalation administration.

The compounds of the present invention can be incorporated into suitable pressure propellants such as dichlorodifluoromethane, propane, nitrogen and the like. In addition, the compounds can be incorporated into suppositories by mixing with a variety of bases, such as emulsifying bases or water-soluble bases. The compounds of the present invention can be administered rectally using a suppository.

A suppository may contain excipients, such as cocoa butter, carboax, and polyethylene glycols, which melt at body temperature but are solid at room temperature. Standard dosage forms for oral or rectal administration, such as syrups, elixirs and suspensions, where each unit dose, for example, a teaspoon, tablespoon, tablet or suppository, may contain a predetermined amount of a composition containing one or more compounds of the present invention.

Similarly, unit dosage forms for injection or intravenous administration may contain the compound of the present invention in the composition in the form of a solution in sterile water, normal saline, or another pharmaceutically acceptable carrier. Implants for sustained release of compositions are well known in the art. Implants are made in the form of microspheres, plates, and so on with biodegradable or non-biodegradable polymers.

For example, polymers of lactic and/or glycolic acid form a degradable polymer that is well tolerated by the host. An implant containing the anti-cancer MATP of the invention is positioned close to the tumor, so that the local concentration of the active agent is increased compared to other areas of the body.

As used herein, the term "unit dosage form" it refers to physically discrete units suitable for use as single doses for human and animal subjects, each unit containing a predetermined number of compounds of the present invention, which, according to calculations, is sufficient to provide the desired effect together with a pharmaceutically acceptable diluent, carrier or excipient.

The descriptions of the unit dosage forms of the present invention depend on the particular compound used, and the effect to be achieved, and the pharmacodynamics of the compound used in the host. Pharmaceutically acceptable excipients, such as excipients, adjuvants, carriers or diluents, are generally available. In addition, pharmaceutically acceptable excipients, such as pH adjusting agents and buffering agents, tonicity agents, stabilizers, wetting agents and the like, are generally available.

Typical doses for systemic administration range from 0.1 pg to 100 milligrams per kg of subject body weight per administration. A typical dose may be one tablet for administration from two to six times a day, or one capsule or sustained release tablet for administration once a day with a proportionally higher content of the active ingredient.

The effect of prolonged release may be due to the materials of which the capsule is made, dissolving at different pH values, capsules providing a slow release under the influence of osmotic pressure or any other known controlled release method. It will be clear to those skilled in the art that dose levels may vary depending on the particular compound, the severity of the symptoms, and the subject's predisposition to side effects. Some of the specific compounds are more potent than others.

Preferred doses of this compound can be readily determined by those skilled in the art in a variety of ways. A preferred method is to measure the physiological activity of the compound. One of the methods of interest is the use of liposomes as a vehicle for delivery.

Liposomes fuse with the cells of the target region and ensure the delivery of liposome contents into the cells. The contact of the liposomes with the cells is maintained for a time sufficient for fusion, using various methods of maintaining contact, such as isolation, binding agents and the like. In one aspect of the invention, liposomes are designed to produce an aerosol for pulmonary administration.

Liposomes can be made with purified proteins or peptides that mediate membrane fusion, such as Sendai virus or influenza virus and so on. Lipids may be any useful combination of known liposome forming lipids, including cationic or zwitterionic lipids, such as phosphatidylcholine. The remaining lipids will usually be neutral or acidic lipids, such as cholesterol, phosphatidylserine, phosphatidylglycerol and the like.

To obtain liposomes, the method described by Kato et al. (1991) J. Biol. Chem. 266: 3361. Briefly, lipids and a composition for incorporation into liposomes containing MATP are mixed in a suitable aqueous medium, suitably in a salt medium, where the total solids content will be in the range of about 110 wt. %. After vigorous stirring for short periods of approximately 5-60 seconds, the tube is placed in a warm water bath at approximately 25-40° C. and this cycle is repeated approximately 5-10 times.

The composition is then sonicated for a suitable period of time, typically approximately 1-10 seconds, and optionally further mixed with a vortex mixer. Then the volume is increased by adding an aqueous medium, usually increasing the volume by about 1-2 times, followed by agitation and cooling. The method allows to include supramolecular structures with high total molecular weight in liposomes.

Compositions with Other Active Agents

To use this methods under consideration, the MATR can be formulated with other pharmaceutically active agents, in particular other anti-cancer, immunomodulatory, wound healing, antiviral agents.

Other agents of interest include a wide range of unmodified drugs known in the art, including antibiotics. Classes of antibiotics include penicillins, for example, penicillin G, penicillin V, methicillin, oxacillin, carbenicillin, nafcillin, ampicillin and so on; penicillins in combination with beta-lactamase inhibitors; cephalosporins, for example, cefaclorome, cefazaliminum, cefazolemine, cefazolemine, cefazolemine, cefazolemine, monobactams; aminoglycosides; tetracyclines; macrolides; lincomycins; polymyxins; sulfonamides; quinolones; chloramphenicol; metronidazole; spectinomycin; trimethoprim; vancomycin; and so on.

Antifungal agents are also useful, including polyenes, for example, amphotericin B, nystatin, flucosin; and azoles, for example miconazole, ketoconazole, itraconazole and fluconazole. Anti-TB drugs include isoniazid, ethambutol, streptomycin and rifampin.

Other agents of interest include a wide range of antiviral derivatives of mononucleotides and other RNA polymerase inhibitor agents known in this type approach.

Classes of antiviral agents include interferons, lamivudine, ribavirin, etc; amantadine; remantadine, for example, zinamivir, oseltavimir and so on; acyclovir, valacyclovir, valganciclovir; and etc.

Other groups of antiviral agents include adefovir, wbacavir, didanosine, emtricitabine, lamivudine, stavudine, tenofovir, efavirenz, nevirapine, indinavir, lopinavir and ritonavir, nelfinavir, ritonavir, sakinavir, daclatasvir, sovofbuvir.

Cytokines, for example, interferon gamma, alpha tumor necrosis factor, interleukin 12, and so on, may also be included in the MATR composition of the invention.

The present invention is further described by the following examples, which should not be construed as limiting the scope of the invention.

INDUSTRIAL APPLICABILITY

The invention relates to organic chemistry and can be used in cosmetology, pharmaceutical and the chemical industry to create new, more effective cosmetic, pharmaceutical compositions, pesticides, acaricides and herbicides based on complementary combinatorial protected RNA oligonucleotides. Therefore, the products obtained based on our invention are completely environmentally friendly, biodegradable and fully metabolizable both in the body and in the environment, and the technologies for their preparation belong to the group of completely waste-free. The production of such products is feasible on the existing equipment of chemical, pharmaceutical and cosmetic enterprises and does not require unique equipment. The raw material base is available and does not require additional efforts for cultivation or production.

The invention claimed is:

1. A biologically active composition comprising a plurality of combinatorial derivatives of a mixture of RNA oligonucleotides obtained by combinatorial carboxylation and formylation of exocyclic amino groups of adenine, guanine, cytosine and ribose alcohol residues of the mixture of RNA oligonucleotides.

2. The biologically active composition according to claim 1, characterized in that the reagents for the combinatorial carboxylation and formylation reactions are used in a molar ratio calculated according to formulae:

$$k = n \times (2^n - 1) \quad (1)$$

$$m = 4 \times (3 \times 2^{n-2} - 1) \quad (2)$$

wherein n=a number of groups available for substitution in an original oligonucleotide;

m=a number of moles of the original oligonucleotide for introduction into the carboxylation and formylation reactions and the number of different molecules of combinatorial derivatives of the original oligonucleotide after the carboxylation and formylation reactions; and k=a number of moles of each of the reagents for the combinatorial carboxylation and formylation reactions.

3. The biologically active composition according to claim 1, wherein the carboxylation of the exocyclic amino groups of nucleosides A, G, C and the alcohol residue of ribose of the mixture of RNA oligonucleotides is carried out by acylation with dicarboxylic acid anhydride.

4. The biologically active composition according to claim 1, wherein the carboxylation of the exocyclic amino groups of nucleosides A, G, C and the alcohol residue of ribose of the mixture of RNA oligonucleotides is carried out by acylation with tricarboxylic acid anhydride.

5. The biologically active composition according to claim 1, wherein the carboxylation of the exocyclic amino groups of nucleosides A, G, C and the alcohol residue of the ribose of the mixture of RNA oligonucleotides is carried out by alkylation with monochloracetic acid.

6. The biologically active composition according to claim 1, wherein the formylation of exocyclic amino groups of nucleosides A, G, C and the alcohol residue of the ribose of the mixture of RNA oligonucleotides is carried out after a preliminary partial carboxylation of the mixture of RNA oligonucleotides.

7. The biologically active composition according to claim 1, wherein the formylation of exocyclic amino groups of nucleosides A, G, C and the alcohol residue of the ribose of the mixture of RNA oligonucleotides is carried out before a partial carboxylation of the mixture of RNA oligonucleotides.

8. The biologically active composition according to claim 1, wherein the formylation and carboxylation of the exocyclic amino groups of nucleosides A, G, C and the alcohol residue of the ribose of the mixture of RNA oligonucleotides are carried out simultaneously by combinatorial synthesis.

9. The biologically active composition according to claim 1, wherein the mixture of RNA oligonucleotides includes RNA oligonucleotides having a nucleotide sequence 3"-UUN1N2N3-5" wherein N1N2N3 correspond to at least one of the following sequences: UUC; UUA; UUG; CUU; CUC; CUA; CUG; AUU; AUC; AUA; AUG; GUU; GUC; GUA; GUG; UCU; UCC; UCA; UCG; CCU; CCC; CCA; CCG; ACU; ACC; ACA; ACG; GCU; GCC; GCA; GCG; UAU; UAC; UAA; UAG; GAU; CAC; GAA; GAG; AAU; AAC; AAA; AAG; GAU; GAC; GAA; GAG; UGU; UGC; UGA; UGG; CGU; CGC; CGA; CGG; AGU; AGC; AGA; AGG; GGU; GGC; GGA; GGG; or a mixture thereof.

10. The biologically active composition according to claim 1, wherein the mixture of RNA oligonucleotide derivatives from the combinatorial carboxylation and formylation reactions includes one or more RNA oligonucleotide derivatives having anticancer activity.

11. The biologically active composition according to claim 1, wherein the mixture of RNA oligonucleotide derivatives from the combinatorial carboxylation and formylation reactions includes one or more RNA oligonucleotide derivatives having regenerative and/or anti-aging activity.

12. The biologically active composition according to claim 1, wherein the mixture of RNA oligonucleotide derivatives from the combinatorial carboxylation and formylation reactions includes one or more RNA oligonucleotide derivatives having acaricidal activity.

13. The biologically active composition according to claim 1, wherein the mixture of RNA oligonucleotide derivatives from the combinatorial carboxylation and formylation reactions includes one or more RNA oligonucleotide derivatives having herbicidal activity.

14. The biologically active composition according to claim 1, wherein the mixture of RNA oligonucleotide derivatives from the combinatorial carboxylation and formylation reactions includes one or more RNA oligonucleotide derivatives having pesticidal activity.

* * * * *